(12) United States Patent
Rubie et al.

(10) Patent No.: US 9,011,554 B2
(45) Date of Patent: Apr. 21, 2015

(54) HIGH-PERFORMANCE MULTI-COMPONENT PROSTHETIC FOOT

(75) Inventors: Eric W. Rubie, Salt Lake City, UT (US); Daniel Buck, Salt Lake City, UT (US)

(73) Assignee: Fillauer Composites LLC, Salt Lake City, UT (US)

( * ) Notice: Subject to any disclaimer, the term of this patent is extended or adjusted under 35 U.S.C. 154(b) by 0 days.

(21) Appl. No.: 12/179,757

(22) Filed: Jul. 25, 2008

(65) Prior Publication Data
US 2010/0023135 A1 Jan. 28, 2010

(51) Int. Cl.
*A61F 2/66* (2006.01)
*A61F 2/50* (2006.01)
*A61F 2/30* (2006.01)

(52) U.S. Cl.
CPC ........... *A61F 2/66* (2013.01); *A61F 2002/5007* (2013.01); *A61F 2002/5086* (2013.01); *A61F 2002/665* (2013.01); *A61F 2/6607* (2013.01); *A61F 2002/30332* (2013.01); *A61F 2002/5055* (2013.01); *A61F 2002/5056* (2013.01); *A61F 2002/6664* (2013.01); *A61F 2002/6671* (2013.01); *A61F 2220/0033* (2013.01)

(58) Field of Classification Search
USPC .............................................. 623/47–55, 56
See application file for complete search history.

(56) References Cited

U.S. PATENT DOCUMENTS

| | | | |
|---|---|---|---|
| 4,007,497 A | 2/1977 | Haupt | |
| 4,605,417 A | 8/1986 | Fleischauer | |
| 4,721,510 A | 1/1988 | Cooper et al. | |
| 4,892,554 A | 1/1990 | Robinson | |
| 5,037,444 A | 8/1991 | Phillips | |
| 5,062,859 A | 11/1991 | Naeder | |
| 5,112,356 A * | 5/1992 | Harris et al. | 623/49 |
| 5,116,384 A | 5/1992 | Wilson et al. | |
| 5,139,525 A | 8/1992 | Kristinsson | |
| 5,156,632 A | 10/1992 | Wellershaus | |
| 5,158,570 A | 10/1992 | Schey et al. | |
| 5,181,932 A | 1/1993 | Phillips | |
| 5,181,933 A | 1/1993 | Phillips | |
| 5,258,038 A | 11/1993 | Robinson et al. | |
| 5,258,039 A | 11/1993 | Goh et al. | |
| 5,290,319 A | 3/1994 | Phillips | |
| 5,376,139 A | 12/1994 | Pitkin | |
| 5,387,246 A | 2/1995 | Phillips | |
| 5,443,528 A | 8/1995 | Allen | |
| 5,507,838 A | 4/1996 | Chen | |
| 5,549,711 A | 8/1996 | Bryant | |
| 5,571,213 A | 11/1996 | Allen | |
| 5,653,767 A | 8/1997 | Allen et al. | |
| 5,695,527 A | 12/1997 | Allen | |
| 5,769,896 A * | 6/1998 | Rosendahl et al. | 623/49 |

(Continued)

FOREIGN PATENT DOCUMENTS

WO    WO 2007/035894 A2    3/2007

*Primary Examiner* — Marcia Watkins
(74) *Attorney, Agent, or Firm* — Chambliss, Bahner & Stophel, P.C.

(57) ABSTRACT

Prosthetic feet are described comprising a curvilinear spring element, including a rounded portion transitioning between upper and lower extensions, the upper extension including a mounting section/region between the curved portion and a distal end of the upper extension. At least one leaf spring element spans a gap between the upper and lower extension sections, and a resilient footbed is attached to the lower extension. Such feet are typically set within a cosmetic cover for and fit within a shoe for use.

18 Claims, 6 Drawing Sheets

(56) References Cited

U.S. PATENT DOCUMENTS

| | | |
|---|---|---|
| 5,776,205 A | 7/1998 | Phillips |
| 5,800,568 A | 9/1998 | Atkinson et al. |
| 5,800,569 A | 9/1998 | Phillips |
| 5,899,944 A | 5/1999 | Phillips |
| 5,944,760 A | 8/1999 | Christensen |
| 6,007,582 A | 12/1999 | May |
| 6,071,313 A | 6/2000 | Phillips |
| 6,077,301 A | 6/2000 | Pusch |
| 6,129,766 A | 10/2000 | Johnson et al. |
| 6,197,066 B1 * | 3/2001 | Gabourie .................. 623/52 |
| 6,197,068 B1 | 3/2001 | Christensen |
| 6,280,479 B1 | 8/2001 | Phillips |
| 6,290,730 B1 | 9/2001 | Pitkin et al. |
| 6,537,322 B1 | 3/2003 | Johnson et al. |
| 6,562,075 B2 | 5/2003 | Townsend et al. |
| 6,572,659 B1 | 6/2003 | Ryan |
| 6,712,860 B2 | 3/2004 | Rubie et al. |
| 6,805,717 B2 | 10/2004 | Christensen |
| 6,911,052 B2 | 6/2005 | Christensen |
| 6,929,665 B2 | 8/2005 | Christensen |
| 6,966,933 B2 | 11/2005 | Christensen |
| 7,060,104 B2 * | 6/2006 | Phillips ..................... 623/55 |
| 7,172,630 B2 | 2/2007 | Christensen |
| 8,034,121 B2 * | 10/2011 | Christensen ............... 623/55 |
| 2005/0033451 A1 | 2/2005 | Aigner et al. |
| 2005/0187640 A1 * | 8/2005 | Christensen ............... 623/52 |
| 2005/0203640 A1 * | 9/2005 | Christensen ............... 623/52 |
| 2006/0069450 A1 * | 3/2006 | McCarvill et al. ......... 623/55 |
| 2007/0100466 A1 * | 5/2007 | Allert ......................... 623/55 |
| 2009/0265019 A1 * | 10/2009 | Chritstensen ............. 623/55 |

* cited by examiner

HIGH-PERFORMANCE MULTI-COMPONENT PROSTHETIC FOOT

BACKGROUND

U.S. Pat. No. 5,156,632 to Wellershaus discloses a jointless prosthetic foot having an S-shaped body. U.S. Pat. No. 6,197,066 to Gabourie discloses yet another one-piece prosthetic foot. It is configured for stop-limited dorsiflexion or dorsiflexion and plantarflexion. A C-shaped "ankle" section is provided that offers a hinge effect until the opening of the shape is closed. At this point, the remainder of the foot is said to be as stiff as possible to facilitate toe-off.

U.S. Pat. No. 5,139,525 to Kristinsson eschews such simplicity in favor of a highly complex mechanical action in which a J-shaped spring attached to a footbed portion includes a snubbing element within the curve of the spring to alter its spring rate. By internal contact of the snubber within the curvature of the spring, corresponding foreshortening of a lower free spring portion occurs to produce increased spring resistance to increased load on the prosthetic foot—and corresponding spring stresses. Such a spring element must be extremely robust.

The present invention bears only an outward resemblance to these designs by way of incorporating what might be seen (in some embodiments) as a J-shaped spring. However, the subject design is implemented in a multi-component construction that avoids features that would introduce problematic stressing leading to bulky spring elements. Accordingly, the present invention is unique in its high performance form and function.

SUMMARY

Employing the features of the present invention, a prosthetic foot is achieved that offers state-of-the-art performance. A unique construction is offered employing a J-shaped curvilinear spring having a portion for attaching a socket mount to an active upper spring region extending forward of the mount, and an active lower spring region extending from a curved portion. These forward-extending regions are spanned by a leaf spring element.

Stated otherwise, prosthetic feet are described as comprising a curvilinear spring element including a rounded portion transitioning between upper and lower extensions, the upper extension including a mounting section between the curved portion and a distal end of the upper extension. At least one leaf spring element spans a gap between the upper and lower extension sections, and a resilient footbed is attached to the lower extension. Such feet are typically set within a cosmetic cover (i.e., a cosmesis) and fit within a shoe for use.

Advantageous configuration(s) are provided in which the curvilinear spring and leaf spring together form a closed loop (e.g., a semi-elliptical shape) around which stress and strain are advantageously distributed in use. The curvilinear spring compresses, with the assistance of the leaf spring, providing a wide range of support and performance tunability as compared to if an elastomeric element were substituted therefore. The interrelated function of the elements allows the system to operate in a larger performance envelope without jeopardizing the structural integrity of the foot, thereby significantly improving the durability. Specifically, it has been appreciated by the inventors hereof that various leaf spring arrangements so employed offer unique performance-tuning opportunities, in an elegant and highly fatigue-resistant manner.

The leaf spring may comprise a linear, curvilinear or elongate form, a U-shape, etc. It may fully or partially span a gap between the upper and lower foot extension sections. It may comprise a unitary element or a plurality of pieces. One or more elastomeric spring elements in addition to (but not in lieu of) the above may be incorporated in the design—especially for fine-tuning. Moreover, active feedback and/or forcing elements may be fit to or incorporated in the design. However, no such elements (active, elastomeric, adjustable air bags, membranes, or otherwise) are required.

Various tuning options are instead achievable by virtue of leaf spring configuration and mode of interaction with other elements. Several preferred foot configurations—each with distinct functionality—are shown and described below. In these, the leaf spring may be connected either proximally, distally or in both locations. Each option produces different performance/tuning opportunities. The leaf spring may be configured to always be in contact with adjacent members, or it may contact them during motion to provide more progressive forcing, thereby allowing a multi-stage loading profile which is superior to single stage conventional designs.

The attachment relation between each of the curvilinear spring and footbed spring elements can, likewise, be varied. So too may be the type of socket attachment mounting/bracket employed for a wearer's stump. However, the bracket mounting point will always reside across the upper extension section of the curvilinear spring, between a cantilevered spring section and a connection between the upper and lower extension sections.

While any or all of the elements are advantageously constructed of carbon fiber composite, various materials may be substituted therefore, particularly spring steel, titanium (e.g., 6-4 titanium alloy), superelastic or SMA Nitinol (i.e., Nickel-Titanium alloy), fiberglass or Kevlar® composite, etc. Making any such substitution is within the ordinary skill of those in the art. The same holds true regarding selection of various mechanical fasteners, composite processing techniques, bonding of elements and/or prosthetic socket interface members.

Beyond such details, the present invention comprises such hardware as shown and described, as well as that more generally embraced by the claims. Moreover, the present invention may include methods of manufacture and ultimate use of the device corollary to the hardware.

BRIEF DESCRIPTION OF THE DRAWINGS

The figures diagrammatically illustrate aspects of the invention. Variation of the invention from that shown in the figures is contemplated, for example, as contemplated in a broader sense in the Summary above. In the variations pictured, similar elements are numbered in like fashion.

DETAILED DESCRIPTION

Figure 1A:
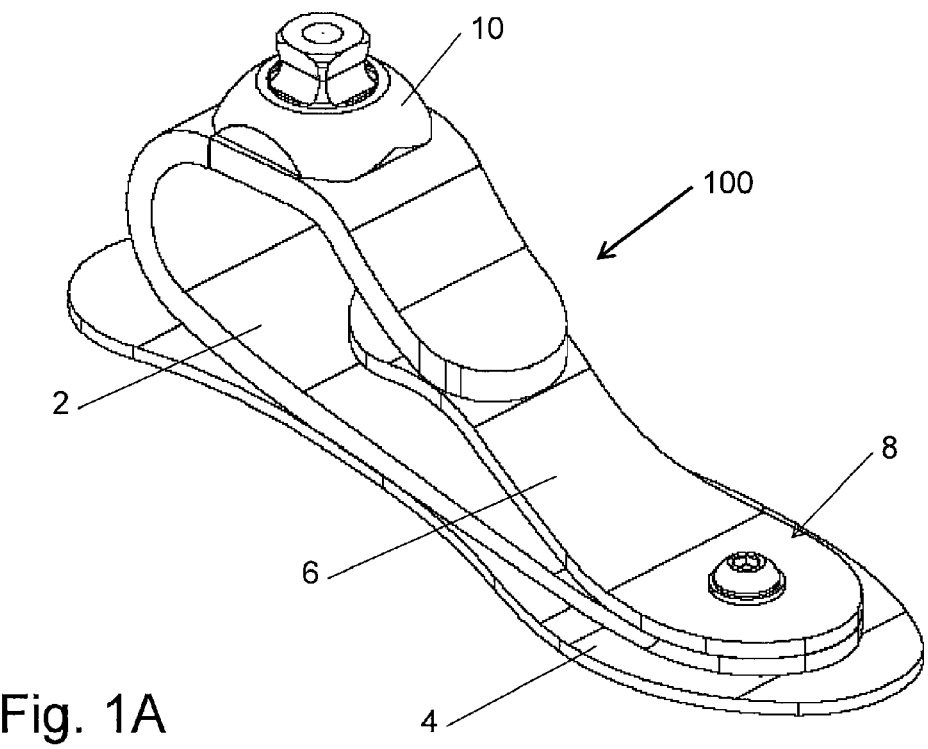
FIGS. 1A and 1B show perspective and side views of one exemplary variation of the present invention.
Figure 1B:
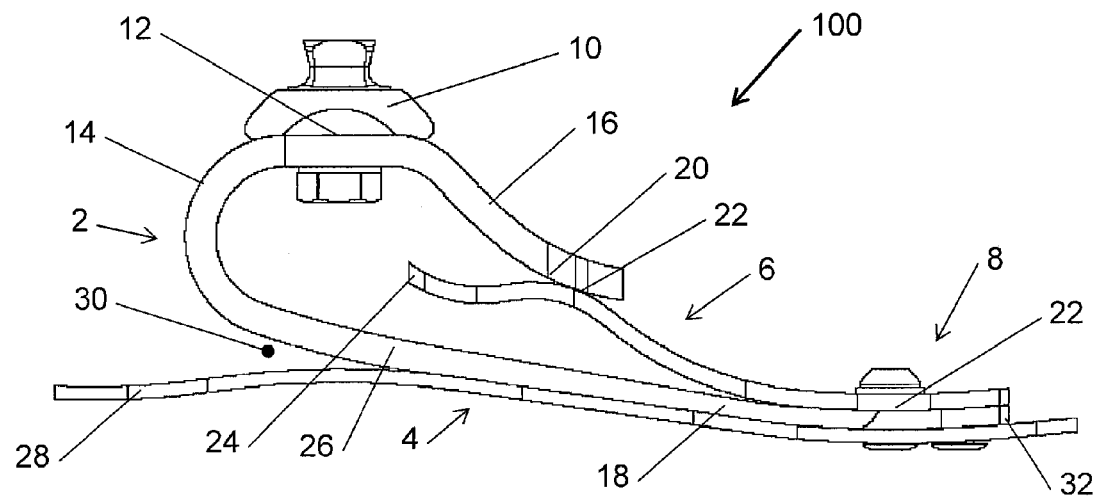

Turning now to FIGS. 1A and 1B, the views illustrate a prosthetic foot 100. In the broadest sense, it includes a primary curvilinear spring element 2, attached to a footbed 4, with a leaf spring element 6. In variation 100, each of curvilinear spring element 2, footbed 4 and leaf spring 6 are joined at a toe-region connection 8.

Curvilinear spring 2 is generally J-shaped and supports a prosthetic socket-mounting bracket 10 (socket not shown).

As seen in FIGS. 1A and 1B, the bracket may be secured (e.g., in a bolted arrangement) across a flat.

An arcuate section 14 connects upper and lower extension sections 16 and 18, respectively. Arcuate section 14 preferably defines a smooth rounded or curved portion for the purpose of flex performance in reaction to force applied by the lever arms defined by extensions 16 and 18. Still, it is to be understood that the rounded portion can be approximated by or incorporate one or more substantially straight and bent/angular sections. Even with such variability, the overall curvilinear spring element will resemble a J or U form and meet the definition of "curvilinear" intended herein—as well as other configurations as may be appreciated by those with skill in the art.

Likewise, leaf spring 6 can take a variety of forms. Also, it can be set up with various end conditions. It may be set up as a cantilevered beam, a simply-supported (dual-end supported) beam, it may transition between such states, it may be compressed in a U shape; etc.

In any case, the leaf spring typically comprises one or more members of metal sheet/plate stock or composite laminate configured as desired. However executed, the exemplary springs spanning the gap between resilient extensions 16 and 18 all meet the definition of a "leaf spring" intended herein—as well as other configurations as may be appreciated by those with skill in the art.

Footbed 4 may be configured as shown. When connected toward its center/middle, it may include a split toe. And in other configurations (e.g., with a toe connection approach as shown in FIGS. 1A and 1B, the heel or substantially all of the footbed may be split—or even comprise side-by-side pieces connected by a plurality of fasteners (see, e.g., FIG. 8B for an attachment arrangement 8 that is suitable for such application). a resilient footbed, the lower extension attached to the footbed.

While FIG. 1A provides an excellent overview of foot 100, the side view in FIG. 1B more clearly illustrates particular aspects. For instance, it clearly shows an upper contact region/zone 20 between leaf spring 6 and upper spring extension 16. Contact over region 20 is made with a convex-up section 22 incorporated in leaf spring 6. A proximal end of the leaf spring incorporates a convex-down section 24 for contact with the lower spring extension along a lower contact region/zone 26 or a bumper (e.g., comprising elastic material such as a hollowed-out polyurethane body, urethane foam, etc.) therebetween. Such a bumper (not shown) can be mounted on either of the leaf spring or opposing surface of the curvilinear spring. Alternatively, both may carry a bumper element.

When no bumper is provided, engagement along the lower region 26 occurs when the curvilinear spring extensions are compressed and the leaf spring deflected. Once this contact is made, the leaf spring is converted from deflecting as a cantilevered element to a simply-supported beam. In doing so, its spring rate increases. The increased spring rate protects the curvilinear spring from unintended strain. Also, it provides a foot that is able to absorb, store and release energy associated with activity including walking, running and jumping.

In support of the referenced engagement, it is noted that the leaf spring may be Teflon®-coated and/or patches of lubricious material adhered (or otherwise affixed) along contact region(s) 20/26 to facilitate sliding motion with the leaf spring. Or as alluded to above, intermediate bumper/elastomeric material may be provided at the various interface regions.

With its unique design, the prosthetic foot permits smooth progression of tibial rotation associated with normal human locomotion. The center of rotation provided coincides with the anatomical ankle joint creating a natural articulation from heel strike to toe-off.

At heel strike, overhanging proximal portion 28 of the footbed flexes along the rounded portion of curvilinear spring 2. At mid-stance, combined flex of the footbed 4 and curvilinear spring 2 permits the tibia to roll forward in a smooth, continuous manner simulating the ankle rocker. Through this progression, the leaf spring compressed between the upper and lower spring extensions 16/18 works to moderate flex to simulate the natural "feel" of ankle rotation while a gap 30 opens as the proximal portion 28 of footplate 4 recovers elastically. During toe-off from a distal end 32 of the prosthetic foot, both the leaf spring and curvilinear spring sections recover to return energy to the user's gait.

In essence, the incorporation of the controlled/controllable progressive flex offered by the leaf spring arrangement serves to avoid the hesitation or "dead spot" that is inherent to many simple cantilever-spring prosthetic foot models. Such designs may offer substantial energy return, but are deficient in the progression from heel-to-toe resistance. The use of the footbed described above offers further assistance in this regard, when it is incorporated in the invention. As such, it provides a useful option.

Accordingly, one aspect of the invention is a method of locomotion with a prosthetic foot comprising loading a substantially U- or J-shaped spring element including upper and lower spring extension sections, transitioning across a footbed attached to the spring element and progressively compressing a leaf spring element between the spring extension sections. The method may further comprise opening a gap between the footbed and the lower extension section during the transitioning to effect additional progressive energy return.

Figure 2:
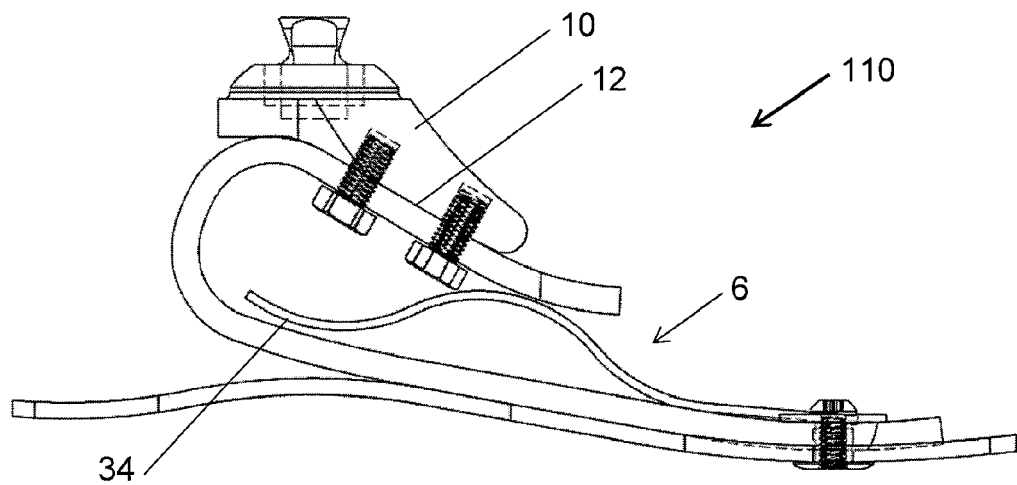
FIGS. 2-7 show side views of additional variations of the invention.

Prosthetic foot 110 as illustrated in FIG. 2 is similar in use and construction to foot 100 with the primary exception of a longer leaf spring 6. With an extended proximal end 34, the amount of compression in the foot prior to the leaf spring being fully supported is decreased or eliminated. Such a design does not leverage the multiple spring rate opportunity afforded in the approach shown in FIGS. 1A and 1B, but it does avoid associated impact, potential "clicking" sound and can still be tuned to achieve desirable performance—if not necessarily through the range of the previous design.

Another difference may also be observed in connection with the mounting bracket 10 and associated mounting region 12. Region 12 offers a smooth transition curve within spring 2 (shown in FIG. 15). This may be desirable from the perspective of performance—especially fatigue—but does complicate the mounting bracket affixation.

Figure 3:
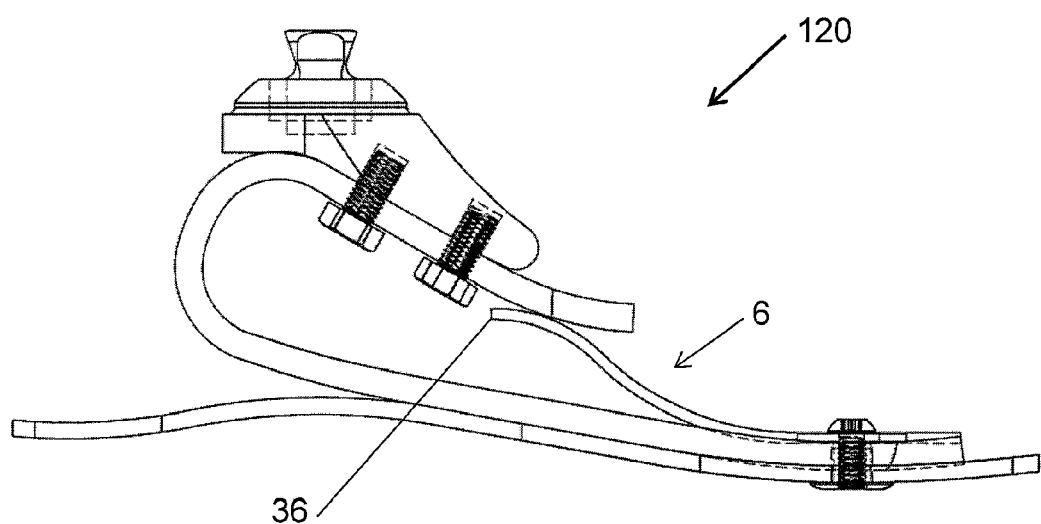

Prosthetic foot 120 as illustrated in FIG. 3 deviates from the design in FIGS. 1A and 1B in that the leaf spring terminates at a proximal point 36 designed to avoid contact with the lower spring extension. In this fashion, the leaf spring is loaded in cantilever-beam fashion throughout its travel. While such an approach offers less potential spring force, it eliminates any possibility of a dead spot from occurring and allows a smooth, continuous rollover without reaching a hard stop. Adopting such a setup may be desirable in down or de-tuning a foot arrangement as shown in FIG. 2 for a lighter user, or one less inclined to high-impact activity.

Figure 4:
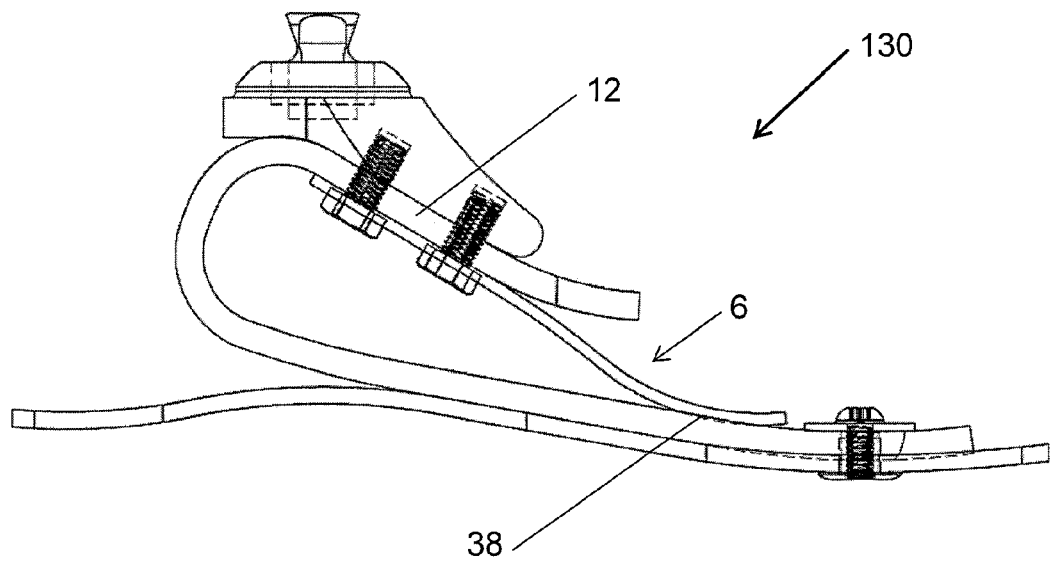

Prosthetic foot 130 as illustrated in FIG. 4 operates much like prosthetic foot 120, except that leaf spring 6 is connected along mounting section 12 with a free-end 38 of the leaf spring directed distally. Such a configuration inherently advantageously accounts for any bolt-clearance issues.

Although the leaf spring is arranged in cantilever fashion as in foot 120, its performance parameters differ.

Figure 5:
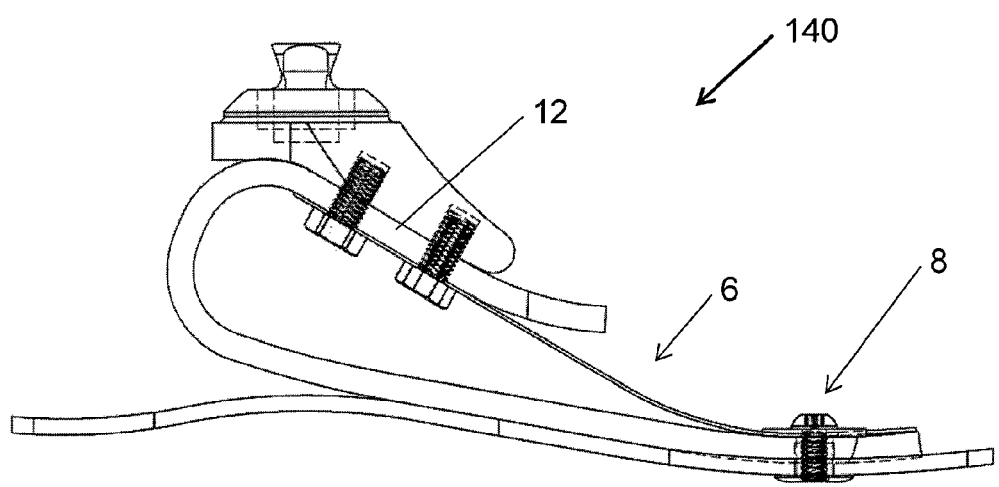

Prosthetic foot 140 as illustrated in FIG. 5 looks similar to prosthetic foot 130, but by connecting both ends of the leaf spring at sections 8 and 12, very different spring performance is achieved. By eliminating the sliding of the leaf spring that can occur along a contact region at one end of the spring, a beam/tension spring element is offered. Namely, the spring will resist bending, but also limits the relation between the curvilinear spring's upper and lower sections. In so doing, a higher spring rate is achieved, thus providing increased dynamic response, and can be utilized in optimizing desired performance generally and/or on a custom basis for a given user. Indeed, the rigidity of the leaf spring 6 shown in FIG. 5 can be varied from a modulus of spring steel, downward. In the most extreme example, the leaf spring serves as a tensioning member that prevents the upper section from fully closing whilst providing a durable design.

Figure 6:
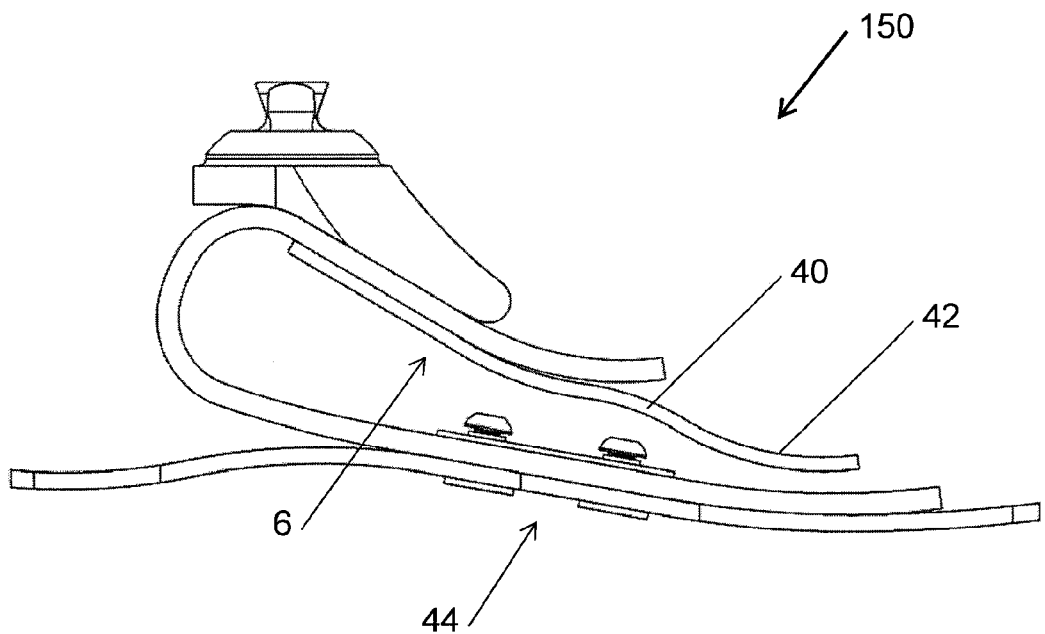

Prosthetic foot 150 as illustrated in FIG. 6 employs a cantilevered spring arrangement similar to that shown in FIG. 5. However, leaf spring 6 is modified with a concave-up section 40 proximal to end 42 of the spring in order to provide clearance for a central/medial mounting section 44 of the footbed and lower spring extension.

Figure 7:
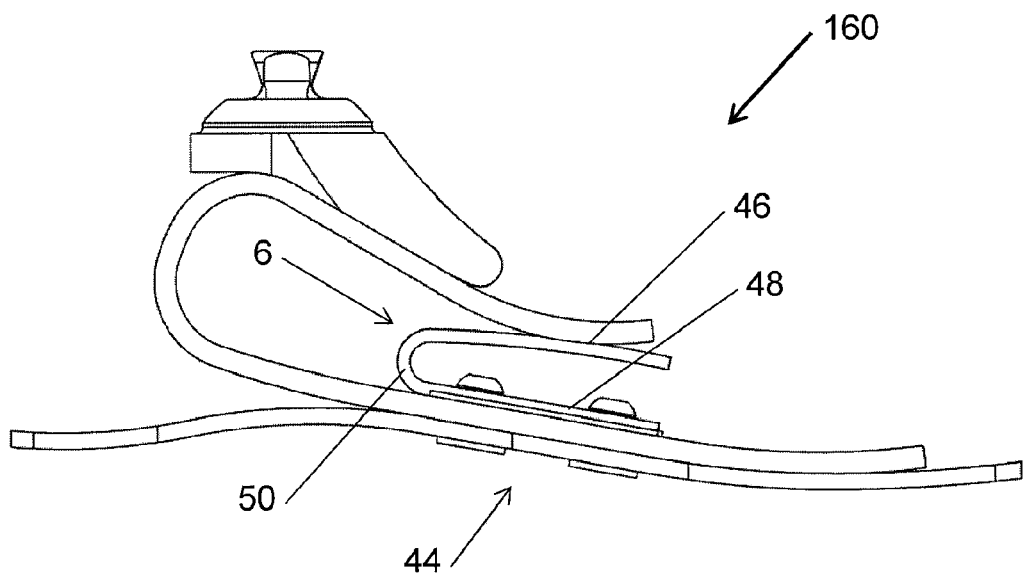

Prosthetic foot 160 as illustrated in FIG. 7 utilized a similar medial connection region 44. However, leaf spring 6 is configured in a C or U shape. Somewhat resembling curvilinear spring 2, it includes upper and lower spring extensions 46/48 and a rounded connection region 50. As shown, the opening of the leaf spring is directed forward/distally. Yet, it can also be set to face rearward/proximally.

Figure 8A:
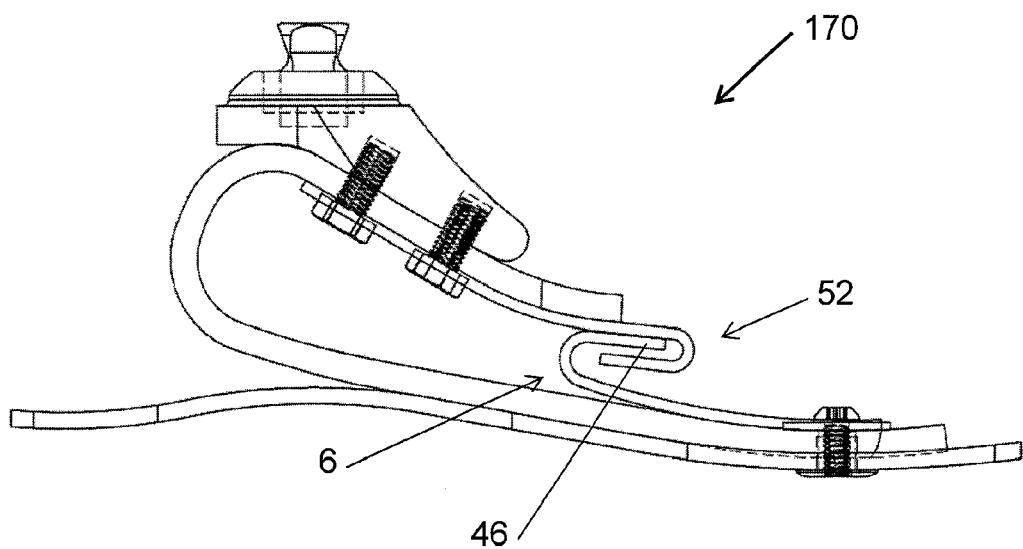
FIGS. 8A and 8B show side and perspective view of the final exemplary variation of the present invention.
Figure 8B:
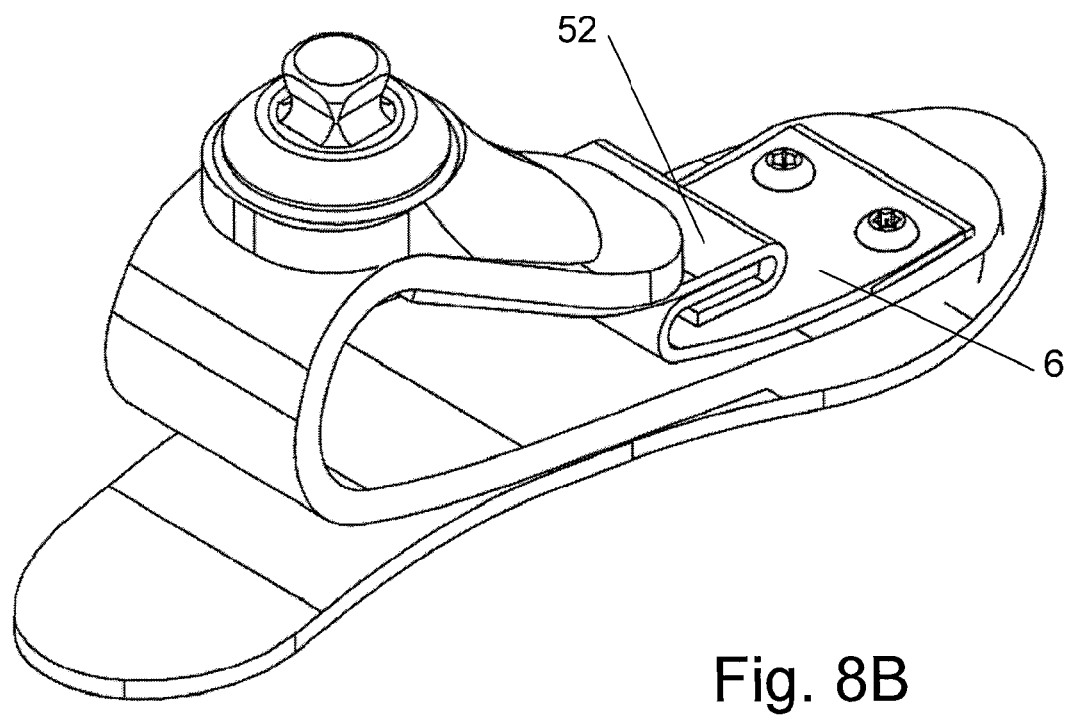

Prosthetic foot 170 as illustrated in FIGS. 8A and 8B includes a rearward facing leaf spring 6 with a U-shaped end. Upper spring extension 46 may offer a more controlled plantar-flexion and dorsi-flexion as the spring elements continue to interact. The joint may include an elastomeric material in the lock or catch member 52 to improve the progression to toe-off and return of the foot to a neutral state.

Variations

Exemplary aspects of the invention, together with details regarding material selection and manufacture have been set forth above. As for other details of the present invention, these may be appreciated in connection with the above-referenced patents and publications as well, as is generally known or appreciated by those with skill in the art. The same may hold true with respect to method-based aspects of the invention in terms of additional acts as commonly or logically employed. Regarding such methods, including methods of manufacture and use, these may be carried out in any order of the events which is logically possible, as well as any recited order of events.

Furthermore, where a range of values is provided, it is understood that every intervening value, between the upper and lower limit of that range and any other stated or intervening value in the stated range is encompassed within the invention. Also, it is contemplated that any optional feature of the inventive variations described may be set forth and claimed independently, or in combination with any one or more of the features described herein.

Though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention.

Reference to a singular item includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject items in the description above, as well as the claims below. It is further noted that the claims may be drafted to exclude any optional element. As such, this statement is intended to serve as an antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim—or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language.

That being said, we claim:

1. A prosthetic foot assembly comprising:
a single, continuous, generally J-shaped curvilinear spring element including a rounded portion transitioning between upper and lower spring extensions, the upper spring extension including a mounting region between the rounded portion and a distal end of the upper spring extension and the rounded portion traversing greater than 180° between the upper and lower spring extensions;
at least one separate and physically distinct leaf spring spanning a gap defined by a distance between a lower surface of the upper spring extension and an upper surface of the lower spring extension, said at least one leaf spring having a toe region and a proximal end, said proximal end including an upper spring extension contact region adapted to slidingly contact the upper spring extension and said toe region being disposed above and fixedly attached to the lower spring extension of the generally J-shaped curvilinear spring element; and
a resilient footbed, the lower spring extension being disposed above and attached to the footbed and said footbed having a heel portion which is adapted to flex upon heel strike.

2. The assembly of claim 1, wherein the leaf spring has an elongate form.

3. The assembly of claim 1, wherein the leaf spring slidingly contacts the upper spring extension.

4. The assembly of claim 1, wherein the leaf spring is bow-shaped.

5. The assembly of claim 1, wherein the proximal end of the leaf spring is spaced apart from the lower spring extension.

6. The assembly of claim 1, wherein the footbed is attached to a distal end of the prosthetic foot.

7. The assembly of claim 1, wherein the leaf spring fully spans the gap.

8. The assembly of claim 1, wherein a socket mounting bracket is connected at the mounting region.

9. The assembly of claim 1 wherein the at least one leaf spring includes a lubricious material.

10. The assembly of claim 9 wherein the lubricious material is provided in the upper spring extension contact region of the at least one leaf spring.

11. The assembly of claim 1 wherein the at least one leaf spring is coated with polytetrafluoroethylene.

12. The assembly of claim 1 wherein the upper spring extension contact region of the at least one leaf spring includes a convex-up section.

13. The assembly of claim 12 wherein the convex-up section is adapted to slidingly contact the upper spring extension.

14. The assembly of claim 13 wherein the convex-up section is provided with a lubricious material.

15. The assembly of claim 1 wherein the proximal end of the at least one leaf spring includes a convex-down section.

16. The assembly of claim 15 wherein the convex-down section is adapted to slidingly contact the lower spring extension.

17. The assembly of claim 16 wherein the convex-down section is provided with a lubricious material.

18. The assembly of claim 1 wherein the generally J-shaped curvilinear spring element is provided with a lubricious material.

* * * * *